(12) United States Patent
Bis et al.

(10) Patent No.: US 9,809,548 B2
(45) Date of Patent: Nov. 7, 2017

(54) POLYMORPHIC FORMS OF THE SODIUM SALT OF 4-TERT-BUTYL-N-[4-CHLORO-2-(1-OXY-PYRIDINE-4-CARBONYL)-PHENYL]-BENZENE SULFONAMIDE

(71) Applicant: ChemoCentryx, Inc., Mountain View, CA (US)

(72) Inventors: Joanna Bis, Cary, NC (US); David H. Igo, Research Triangle Park, NC (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 15/289,629

(22) Filed: Oct. 10, 2016

(65) Prior Publication Data
US 2017/0022161 A1 Jan. 26, 2017

Related U.S. Application Data

(62) Division of application No. 14/832,755, filed on Aug. 21, 2015, now Pat. No. 9,493,417, which is a division of application No. 14/234,279, filed as application No. PCT/US2012/047513 on Jul. 20, 2012, now Pat. No. 9,150,513.

(60) Provisional application No. 61/510,559, filed on Jul. 22, 2011.

(51) Int. Cl.
| | |
|---|---|
| C07D 211/82 | (2006.01) |
| C07D 213/89 | (2006.01) |
| A61K 31/44 | (2006.01) |
| A61K 31/4425 | (2006.01) |
| A61K 45/06 | (2006.01) |

(52) U.S. Cl.
CPC ............ *C07D 213/89* (2013.01); *A61K 31/44* (2013.01); *A61K 31/4425* (2013.01); *A61K 45/06* (2013.01); *C07B 2200/13* (2013.01)

(58) Field of Classification Search
CPC .................................................. C07D 213/895
USPC ........................................................ 546/328
See application file for complete search history.

(56) References Cited

U.S. PATENT DOCUMENTS

| | | | | |
|---|---|---|---|---|
| 6,939,885 | B2 | 9/2005 | Ungashe et al. | |
| 9,133,124 | B2 * | 9/2015 | Pennell | C07D 213/89 |
| 9,139,526 | B2 * | 9/2015 | Bis | C07D 213/89 |
| 9,150,513 | B2 * | 10/2015 | Bis | C07D 213/89 |
| 9,464,054 | B2 * | 10/2016 | Bis | C07D 213/89 |
| 9,493,417 | B2 * | 11/2016 | Bis | C07D 213/89 |
| 2004/0038976 | A1 | 2/2004 | Fleming et al. | |
| 2005/0250820 | A1 | 11/2005 | Chen | |
| 2008/0161345 | A1 | 7/2008 | Ungashe et al. | |
| 2010/0234364 | A1 | 9/2010 | Basak et al. | |
| 2011/0118248 | A1 | 5/2011 | Ungashe et al. | |

FOREIGN PATENT DOCUMENTS

| | | |
|---|---|---|
| CN | 1711257 A | 12/2005 |
| CN | 1738796 A | 2/2006 |
| CN | 101077867 A | 11/2007 |
| WO | WO 03/099773 A1 | 12/2003 |
| WO | WO 2004/046092 A2 | 6/2004 |
| WO | WO 2005/113513 A2 | 12/2005 |
| WO | WO 2008/008374 A2 | 1/2008 |

OTHER PUBLICATIONS

Berge, Stephen M., et al., "Pharmaceutical Salts," J. Pharm. Sci. 66(1):1-19 (Jan. 1977).
Brittain, H.G., "Polymorphism in Pharmaceutical Solids," Mercel Dekker, D. J. W.; Grant (chapter 1), pp. 1-10 (1995).
Brittain, H.G., "Polymorphism in Pharmaceutical Solids," Mercel Dekker, D. J. W.; J.K. Guillory (chapter 5), pp. 183-226 (1995).
Byrn, Stephen, et al., "Pharmaceutical Solids: A Strategic Approach to Regulatory Considerations," Pharmaceutical Research 12(7):945-954 (1995).
Caira, Mino R., "Crystalline Polymorphism of Organic Compounds," Topic in Current Chemistry 198:163-208 (1998).
European Medicines Agency, "ICH Topic Q3C(R4) Impurities: Residual Solvents," retrieved from http://www.emea.europa.eu/pdfs/human/ich/013595.en.pdf, pp. 1-22 (2010).
First Office Action for CN Application No. 201280036358.9, dated Jan. 14, 2015 (15 pages).
First Office Action for CN Application No. 201280036359.3, dated Feb. 4, 2015 (8 pages).
Hilfiker, Rolf, et al.: "Chapter 1.4: Phases of Development and Solid-state Research" in Polymorphism in the Pharmaceutical Industry, Wiley-VCH, Weinheim, pp. 7-13 (Jan. 1, 2006).
Hong, Zheng, et al., "Chemokines and receptors thereof and human immune related diseases," Chongqing Medicine 31(8):641-643 (2002).
Hydrate Labs, URL: http://www.chalkbored.com/lessons/chemistry-11/hydrate-lab.pdf. Accessed online May 17, 2008 (3 pages).
International Search Report and Written Opinion of the International Searching Authority for International Application No. PCT/US2012/047512, dated Sep. 28, 2012 (7 pages).
International Search Report and Written Opinion of the International Searching Authority for International Application No. PCT/US2012/047513, dated Sep. 28, 2012 (18 pages).

(Continued)

*Primary Examiner* — Nizal Chandrakumar
(74) *Attorney, Agent, or Firm* — Brinks Gilson & Lione; Ryan L. Marshall

(57) ABSTRACT

Disclosed are novel polymorphic solvated and desolvated forms of the sodium salt of 4-tert-butyl-N-[4-chloro-2-(1-oxy-pyridine-4-carbonyl)phenyl]-benzenesulfonamide. One embodiment of the present invention is directed to a crystalline sodium salt of 4-tert-butyl-N-[4-chloro-2-(1-oxy-pyridine-4-carbonyl)-phenyl]benzenesulfonamide (hereinafter "Compound A-1,4-dioxane/water solvate"), wherein the crystalline form is characterized by an X-ray powder diffraction pattern comprising diffraction angles (°2θ), when measured using Cu Kα radiation, at about 4.0, 8.1, 10.1, 14.2, 16.2, 18.6, 20.3, 24.7, 25.0, and 26.5.

7 Claims, 18 Drawing Sheets

(56) References Cited

OTHER PUBLICATIONS

International Search Report and Written Opinion of the International Searching Authority for International Application No. PCT/US2012/047559, dated Sep. 7, 2012 (11 pages).

Liao, Shao-lan, et al., "Research Progress of new anti AIDS drug—chemokine receptor antagonists," World Notes on Antibiotics 29(2):58-62 (2008).

Stahl, P. Heinrich, "Preparation of Water-Soluble Compounds Through Salt Formation," The Practice of Medicinal Chemistry, 2nd edition, pp. 601-615 (2003).

Supplemental European Search Report for EP Application No. 12817325.9, issued Feb. 2, 2015 (9 pages).

Supplemental European Search Report for EP Application No. 12818186.4, issued Feb. 2, 2015 (9 pages).

West, "Solid-State Chemistry and Its Applications," John Wiley & Sons, 3 pages (1984).

\* cited by examiner

POLYMORPHIC FORMS OF THE SODIUM SALT OF 4-TERT-BUTYL-N-[4-CHLORO-2-(1-OXY-PYRIDINE-4-CARBONYL)-PHENYL]-BENZENE SULFONAMIDE

REFERENCE TO EARLIER FILED APPLICATIONS

This application is a divisional of U.S. application Ser. No. 14/832,755 filed Aug. 21, 2015, which is a divisional of U.S. application Ser. No. 14/234,279, filed Jan. 22, 2014, which is a 371 national phase of PCT/US2012/047513, filed Jul. 20, 2012, and claims the benefit under 35 U.S.C. §119(e) of U.S. Provisional Application No. 61/510,559, filed Jul. 22, 2011, the disclosures of which are incorporated, in their entirety, by this reference.

BACKGROUND OF THE INVENTION

In the pursuit of a developable form of a solid, orally-administered pharmaceutical compound, a number of specific features are sought. Although an amorphous form of a pharmaceutical compound may be developed, compounds having high crystallinity are generally preferred. Often such highly crystalline compounds are salts.

International Publication Number WO 2004/046092 describes a series of compounds which are indicated as antagonists of the CCR9 receptor, and which are indicated as being useful in the treatment of CCR9-mediated disorders. Specifically disclosed in that application is the compound 4-tert-butyl-N-[4-chloro-2-(1-oxy-pyridine-4-carbonyl)-phenyl]-benzenesulfonamide. Identification of a stable, crystalline form of such compound with suitable properties for oral administration would be highly desirable for the treatment of CCR9-mediated diseases.

SUMMARY OF THE INVENTION

The present invention relates to novel polymorphic solvated or desolvated forms of the sodium salt of 4-tert-butyl-N-[4-chloro-2-(1-oxy-pyridine-4-carbonyl)-phenyl]-benzenesulfonamide (hereinafter "Compound A"). The compounds of the invention are represented by Structure (I):

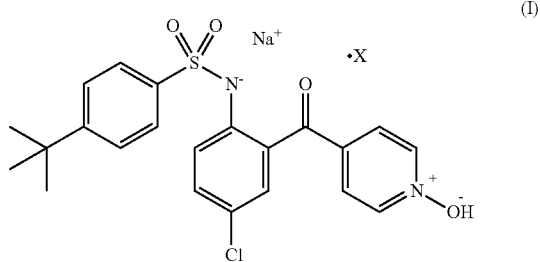

(I)

Specifically, compounds where X is a solvent or solvent mixture such as 1,4-dioxane/water, formamide, dimethylsulfoxide, or water, or where X is absent. The compounds of this invention are useful for antagonizing the CCR9 receptor, and for treating diseases such as inflammatory bowel disease, including Crohn's disease and ulcerative colitis.

DETAILED DESCRIPTION OF THE INVENTION

The present invention is directed to novel polymorphic solvated and desolvated forms of the sodium salt of 4-tert-butyl-N-[4-chloro-2-(1-oxy-pyridine-4-carbonyl)-phenyl]-benzenesulfonamide. One embodiment of the present invention is directed to a crystalline sodium salt of 4-tert-butyl-N-[4-chloro-2-(1-oxy-pyridine-4-carbonyl)-phenyl]-benzenesulfonamide (hereinafter "Compound A—1,4-dioxane/water solvate"), wherein the crystalline form is characterized by an X-ray powder diffraction pattern comprising diffraction angles (°2θ), when measured using Cu K$_\alpha$ radiation, at about 4.0, 8.1, 10.1, 14.2, 16.2, 18.6, 20.3, 24.7, 25.0, and 26.5.

Figure 1:
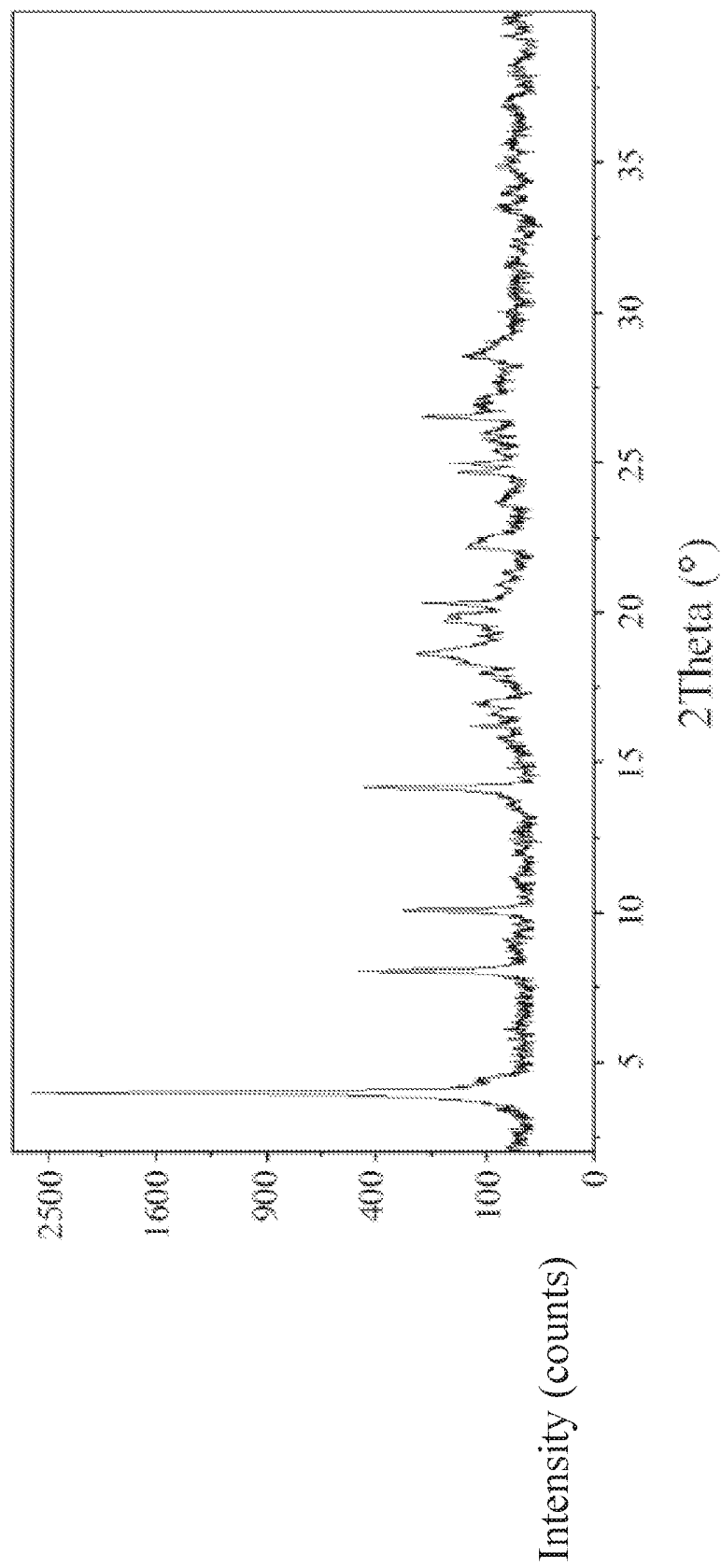
FIG. 1 shows an X-ray powder diffraction pattern of Compound A—1,4-dioxane/water solvate.

Another embodiment of the present invention is directed to Compound A—1,4-dioxane/water solvate, wherein the crystalline form is characterized by an X-ray powder diffraction pattern substantially in accordance with FIG. 1.

Another embodiment of the present invention is directed to Compound A—1,4-dioxane/water solvate, wherein the crystalline form provides a Raman spectrum containing peaks at about 668, 743, 804, 1125, 1154, 162, 1286, 1544, 1587, 1597, 1611, 1657, and 1672 cm$^{-1}$.

Figure 6:
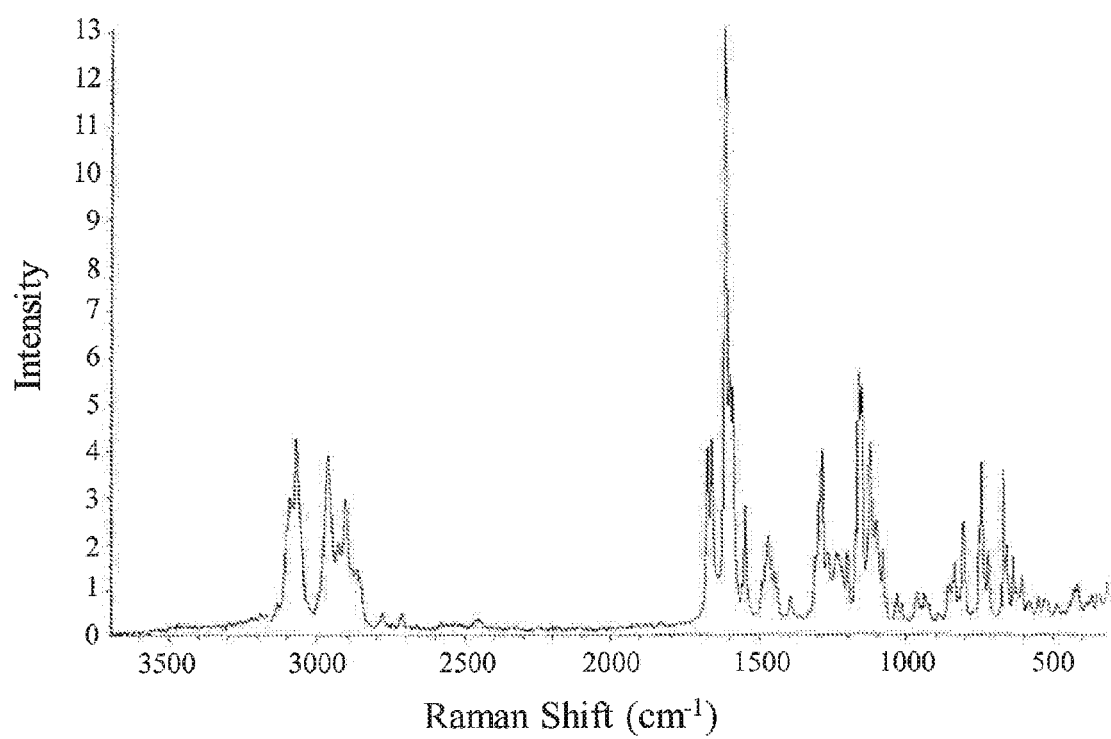
FIG. 6 shows a Raman spectrum of Compound A—1,4-dioxane/water solvate.

Another embodiment of the present invention is directed to Compound A—1,4-dioxane/water solvate, wherein the crystalline form provides a Raman spectrum substantially in accordance with FIG. 6.

Figure 10:
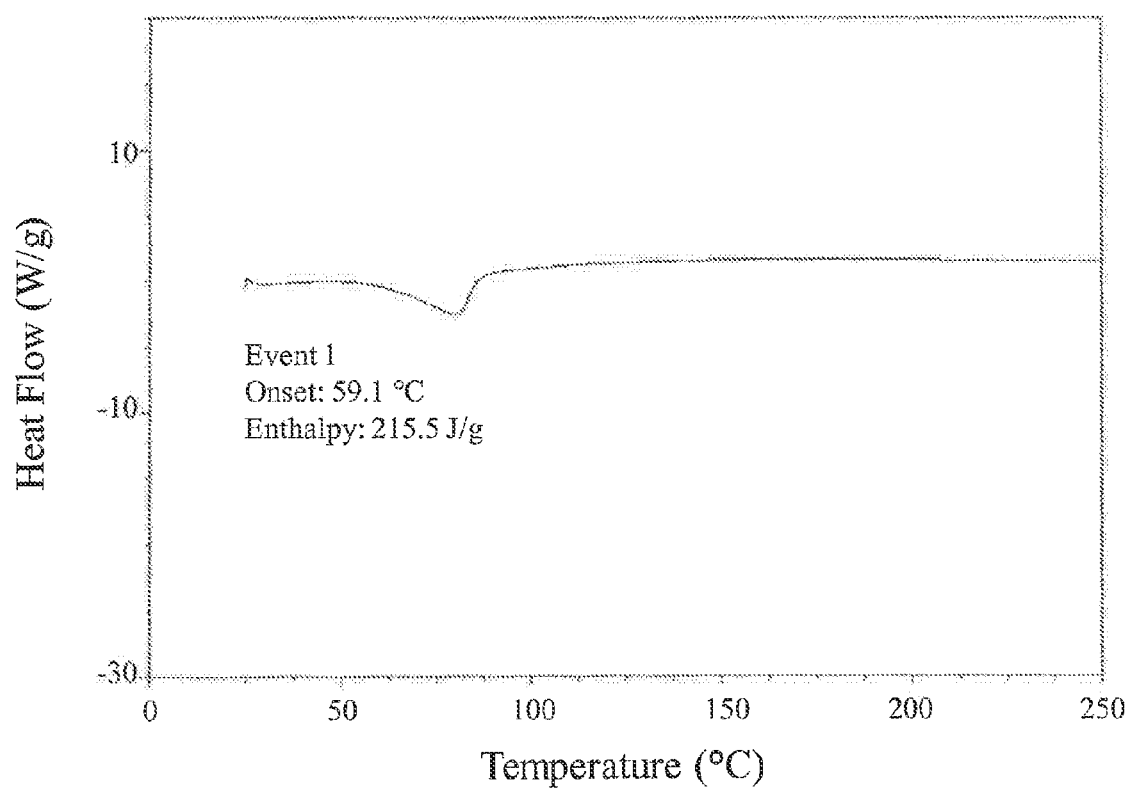
FIG. 10 shows a differential scanning calorimetry trace of Compound A—1,4-dioxane/water solvate.
Figure 14:
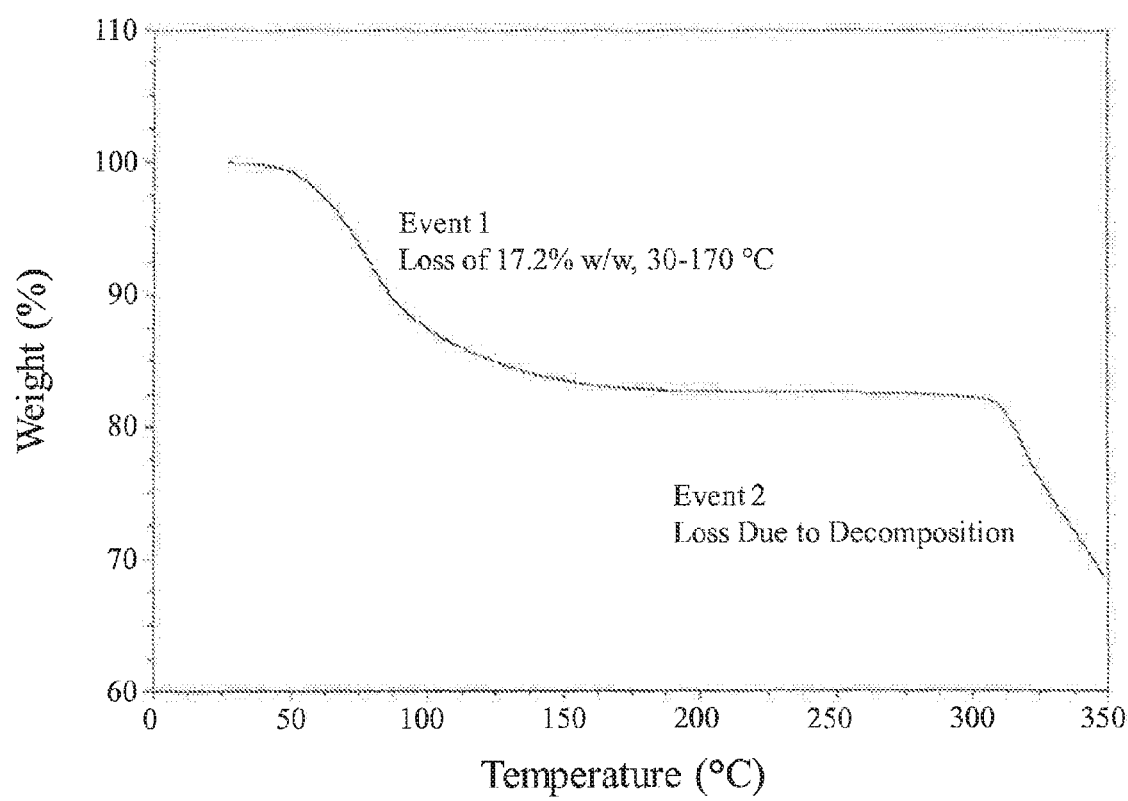
FIG. 14 shows a thermogravimetric analysis trace of Compound A—1,4-dioxane/water solvate.

Another embodiment of the present invention is directed to Compound A—1,4-dioxane/water solvate, wherein the crystalline form provides a differential scanning calorimetry trace substantially in accordance with FIG. 10 and/or a thermogravimetric analysis trace substantially in accordance with FIG. 14.

Another embodiment of the present invention is directed to a crystalline sodium salt of 4-tert-butyl-N-[4-chloro-2-(1-oxy-pyridine-4-carbonyl)-phenyl]-benzenesulfonamide (hereinafter "Compound A—formamide solvate"), wherein the crystalline form is characterized by an X-ray powder diffraction pattern comprising diffraction angles (°2θ), when measured using Cu K$_\alpha$ radiation, at about 5.9, 8.6, 12.1, 12.7, 16.1, 16.9, 17.4, 17.8, 18.0, 20.4, 20.6, 21.7, 22.6, 23.7, 23.9, 24.3, 25.9, 26.3, 26.5, 26.9, 27.9, 30.9, and 38.6.

Figure 2:
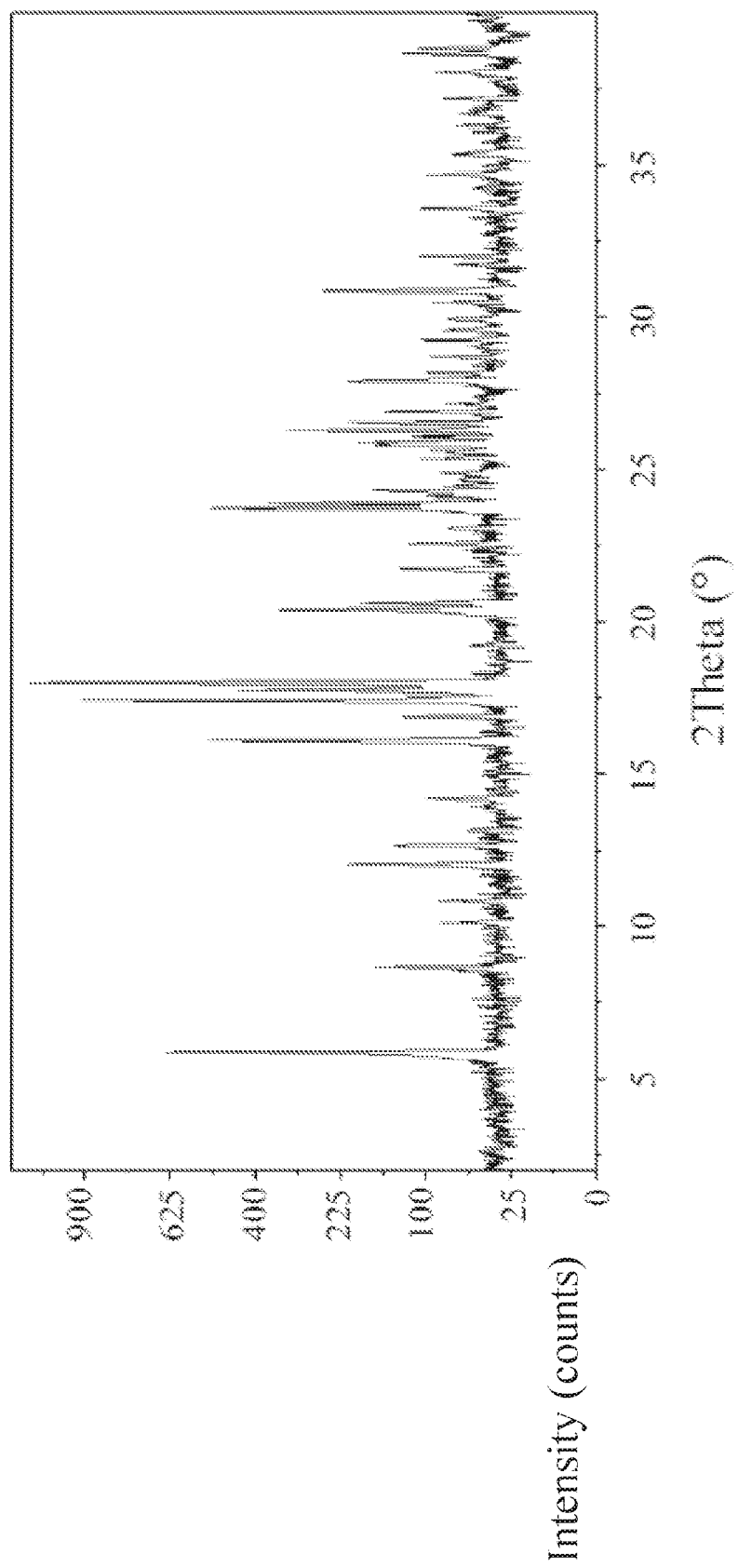
FIG. 2 shows an X-ray powder diffraction pattern of Compound A—formamide solvate.

Another embodiment of the present invention is directed to Compound A—formamide solvate, wherein the crystalline form is characterized by an X-ray powder diffraction pattern substantially in accordance with FIG. 2.

Another embodiment of the present invention is directed to Compound A—formamide solvate, wherein the crystalline form provides a Raman spectrum containing peaks at about 655, 668, 737, 804, 1079, 1099, 1123, 1161, 1229, 1303, 1465, 1537, 1595, 1611, and 1654 cm$^{-1}$.

Figure 7:
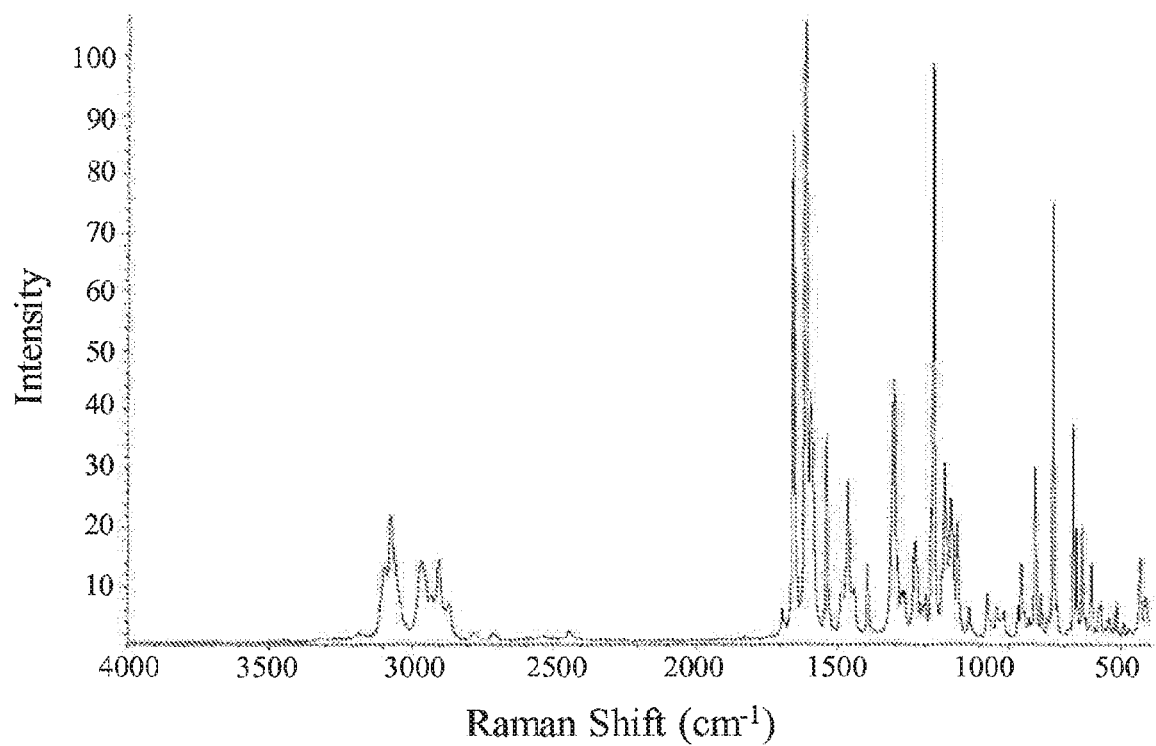
FIG. 7 shows a Raman spectrum of Compound A—formamide solvate.

Another embodiment of the present invention is directed to Compound A—formamide solvate, wherein the crystalline form provides a Raman spectrum substantially in accordance with FIG. 7.

Figure 11:
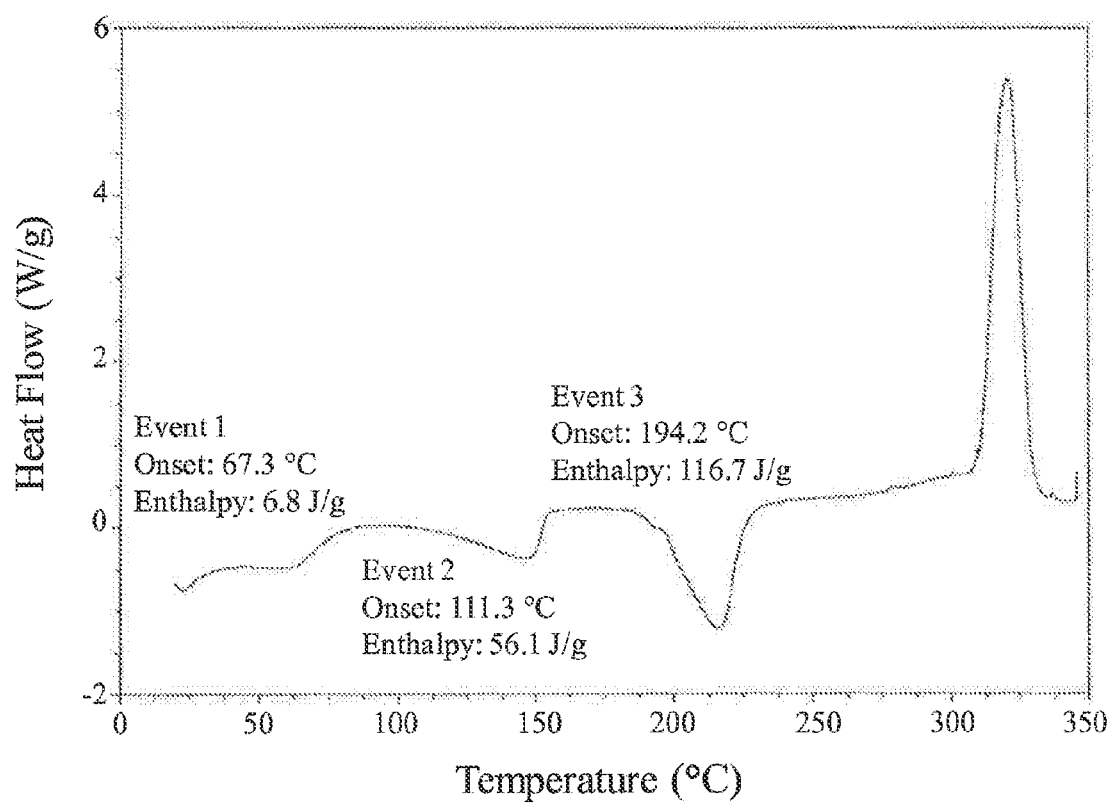
FIG. 11 shows a differential scanning calorimetry trace of Compound A—formamide solvate.
Figure 15:
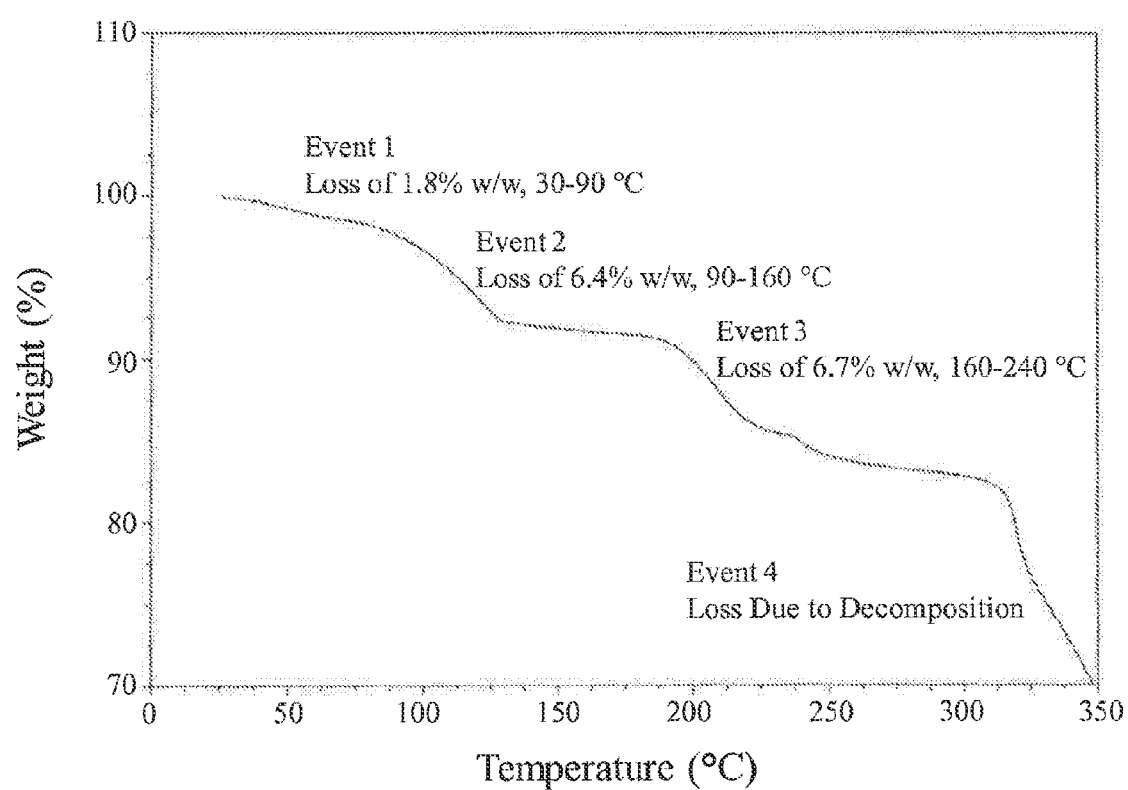
FIG. 15 shows a thermogravimetric analysis trace of Compound A—formamide solvate.

Another embodiment of the present invention is directed to Compound A—formamide solvate, wherein the crystalline form provides a differential scanning calorimetry trace substantially in accordance with FIG. 11 and/or a thermogravimetric analysis trace substantially in accordance with FIG. 15.

Another embodiment of the present invention is directed to a crystalline sodium salt of 4-tert-butyl-N-[4-chloro-2-(1-oxy-pyridine-4-carbonyl)-phenyl]-benzenesulfonamide (hereinafter "Compound A—dimethylsulfoxide solvate"), wherein the crystalline form is characterized by an X-ray powder diffraction pattern comprising diffraction angles (°2θ), when measured using Cu K$_\alpha$ radiation, at about 5.6, 8.0, 10.8, 15.7, 17.0, 17.7, 18.0, 18.1, 18.4, 21.2, 21.8, 22.5, 22.8, 24.3, 28.6, 29.7, and 34.5.

Figure 3:
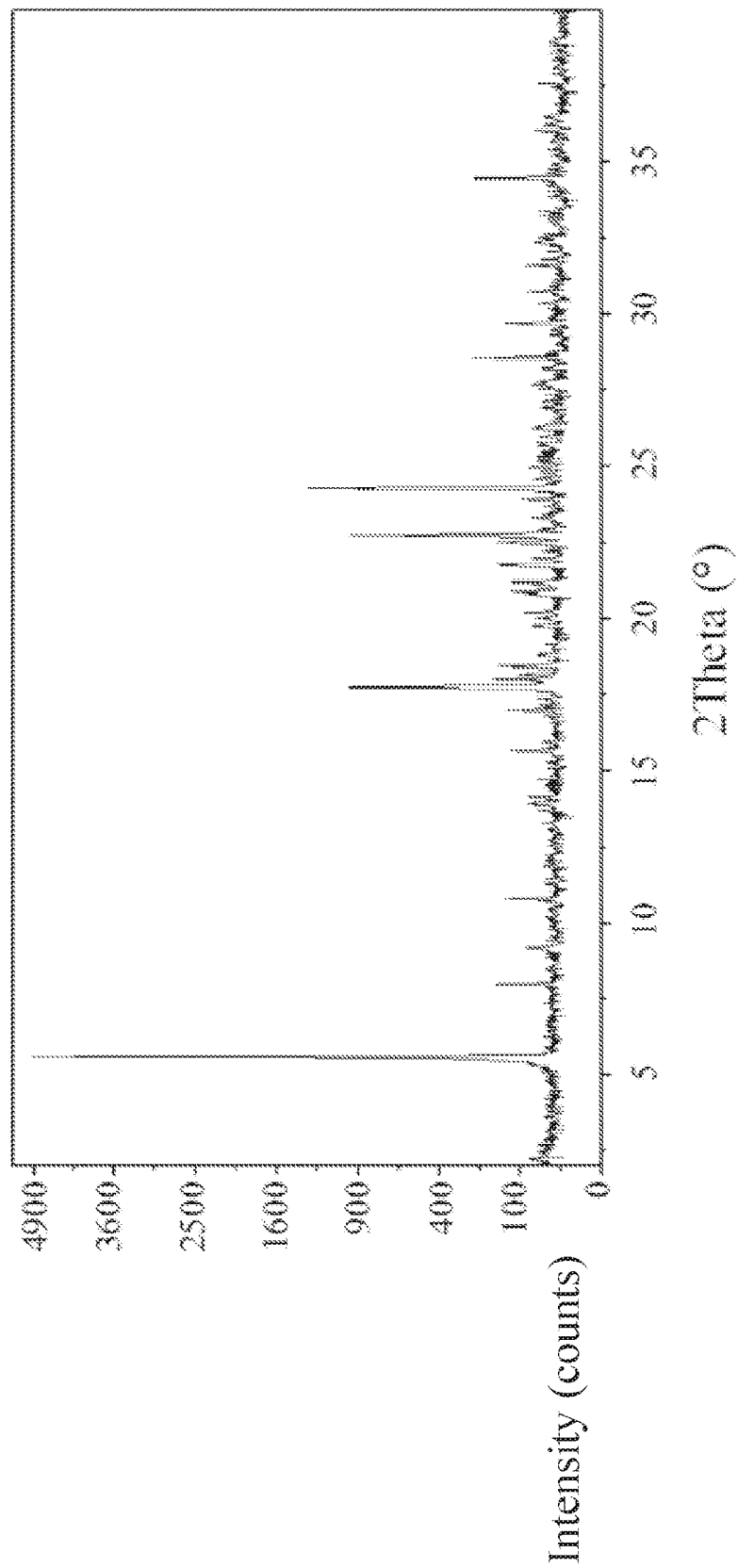
FIG. 3 shows an X-ray powder diffraction pattern of Compound A—dimethylsulfoxide solvate.

Another embodiment of the present invention is directed to Compound A—dimethylsulfoxide solvate, wherein the crystalline form is characterized by an X-ray powder diffraction pattern substantially in accordance with FIG. 3.

Another embodiment of the present invention is directed to Compound A—dimethylsulfoxide solvate, wherein the crystalline form provides a Raman spectrum containing peaks at about 662, 672, 718, 729, 750, 799, 1078, 1109, 1158, 1236, 1302, 1536, 1588, 1596, and 1636 cm$^{-1}$.

Figure 8:
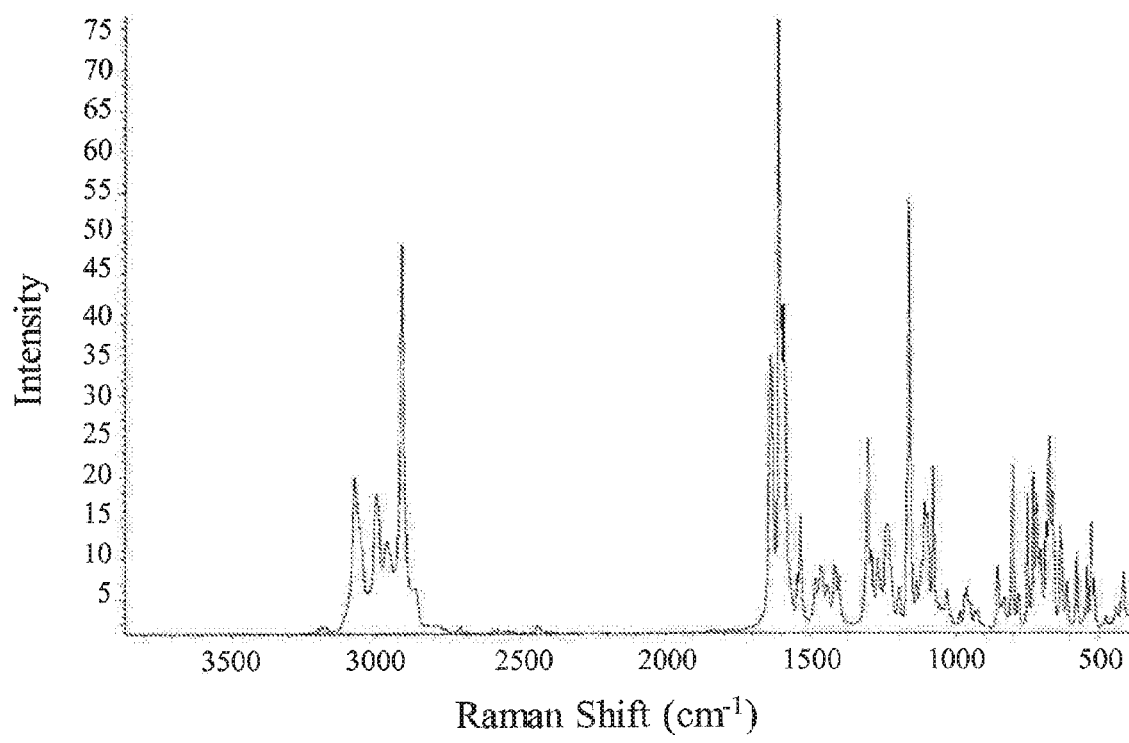
FIG. 8 shows a Raman spectrum of Compound A—dimethylsulfoxide solvate.

Another embodiment of the present invention is directed to Compound Compound A—dimethylsulfoxide solvate, wherein the crystalline form provides a Raman spectrum substantially in accordance with FIG. 8.

Figure 12:
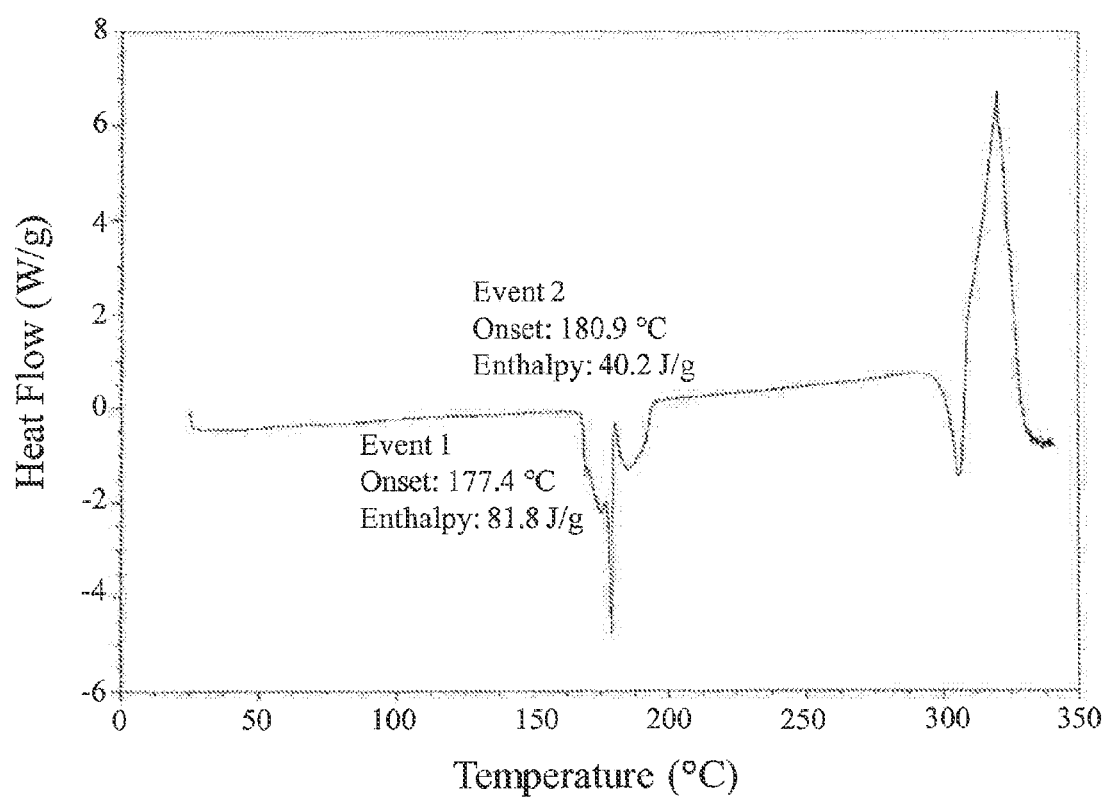
FIG. 12 shows a differential scanning calorimetry trace of Compound A—dimethylsulfoxide solvate.
Figure 16:
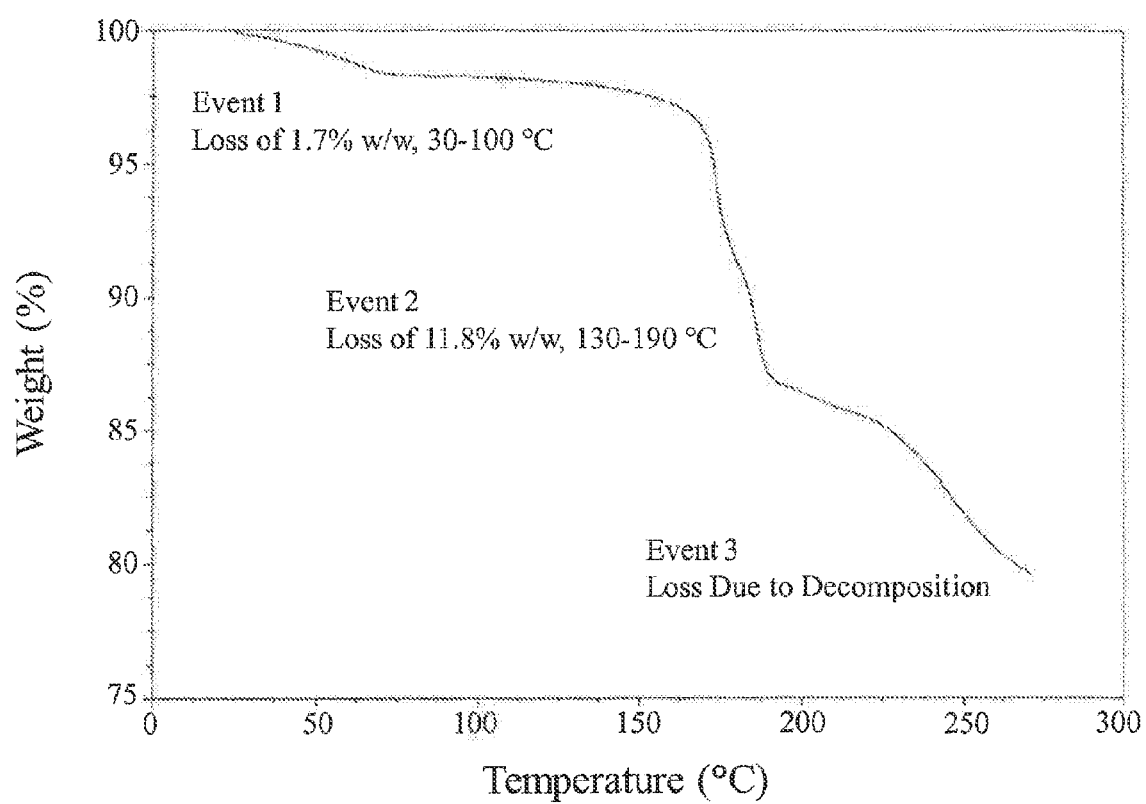
FIG. 16 shows a thermogravimetric analysis trace of Compound A—dimethylsulfoxide solvate.

Another embodiment of the present invention is directed to Compound A—dimethylsulfoxide solvate, wherein the crystalline form provides a differential scanning calorimetry trace substantially in accordance with FIG. 12 and/or a thermogravimetric analysis trace substantially in accordance with FIG. 16.

Another embodiment of the present invention is directed to a crystalline sodium salt of 4-tert-butyl-N-[4-chloro-2-(1-oxy-pyridine-4-carbonyl)-phenyl]-benzenesulfonamide (hereinafter "Compound A—desolvated crystalline form"), wherein the crystalline form is characterized by an X-ray powder diffraction pattern comprising diffraction angles (°2θ), when measured using Cu K$_\alpha$ radiation, at about 6.5, 9.6, 10.6, 11.9, 14.4, 16.1, 17.7, 17.9, 19.3, 21.1, 22.0, 22.2, 23.4, 23.6, 24.4, 26.3, 27.7, 28.5, and 29.5.

Figure 4:
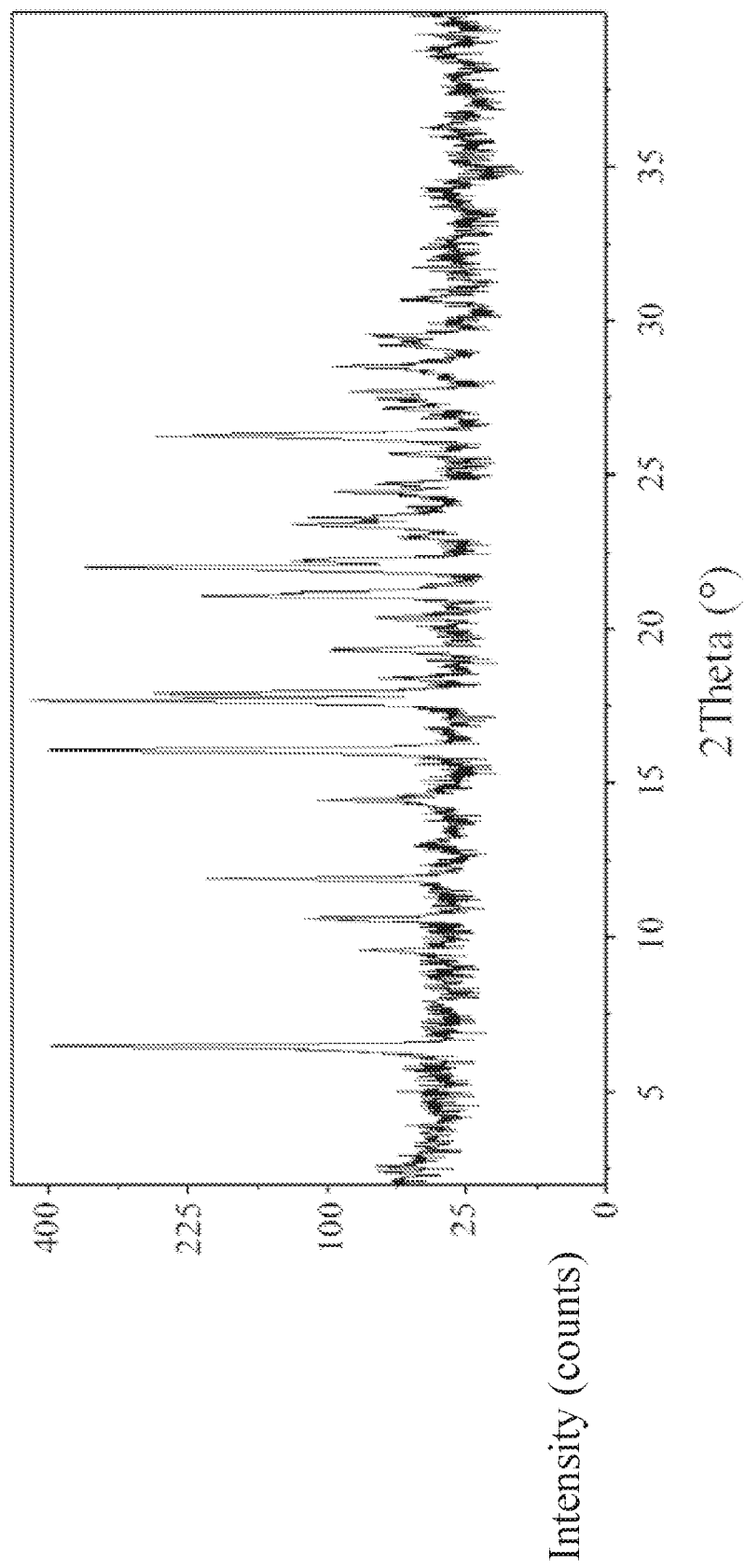
FIG. 4 shows an X-ray powder diffraction pattern of Compound A—desolvated crystalline form.

Another embodiment of the present invention is directed to Compound A—desolvated crystalline form, wherein the crystalline form is characterized by an X-ray powder diffraction pattern substantially in accordance with FIG. 4.

Another embodiment of the present invention is directed to Compound A—desolvated crystalline form, wherein the crystalline form provides a Raman spectrum containing peaks at about 654, 667, 737, 803, 855, 1077, 1122, 1160, 1311, 1461, 1536, 1592, 1609, and 1648 cm$^{-1}$.

Figure 9:
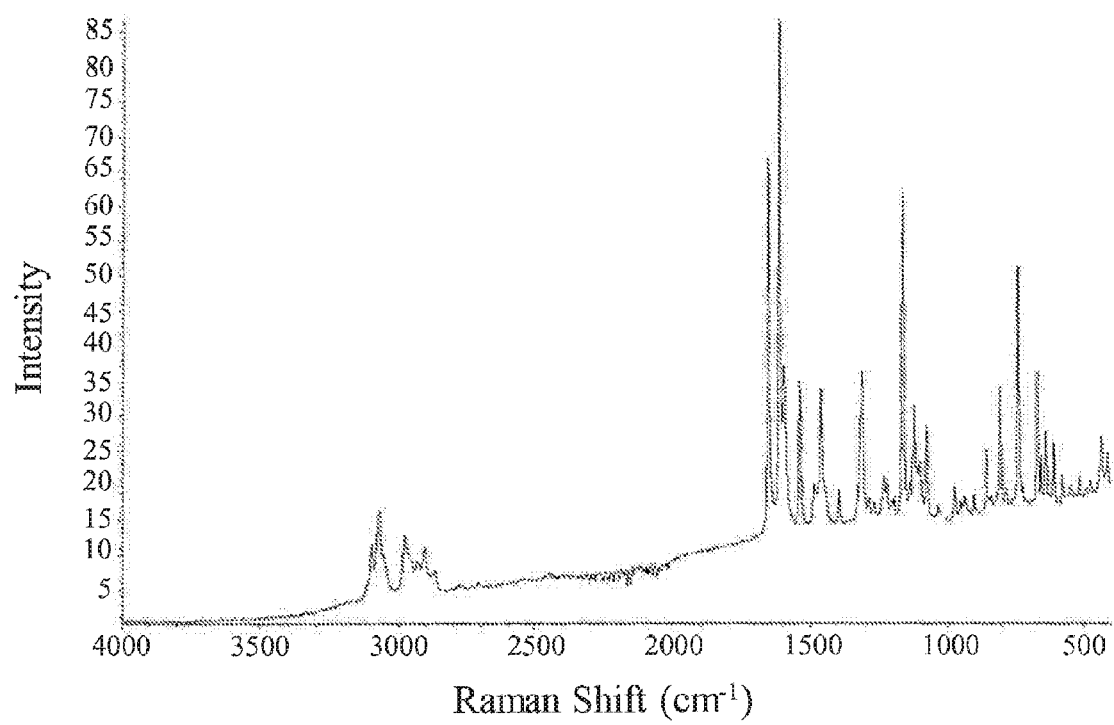
FIG. 9 shows a Raman spectrum of Compound A—desolvated crystalline form.

Another embodiment of the present invention is directed to Compound A—desolvated crystalline form, wherein the crystalline form provides a Raman spectrum substantially in accordance with FIG. 9.

Figure 13:
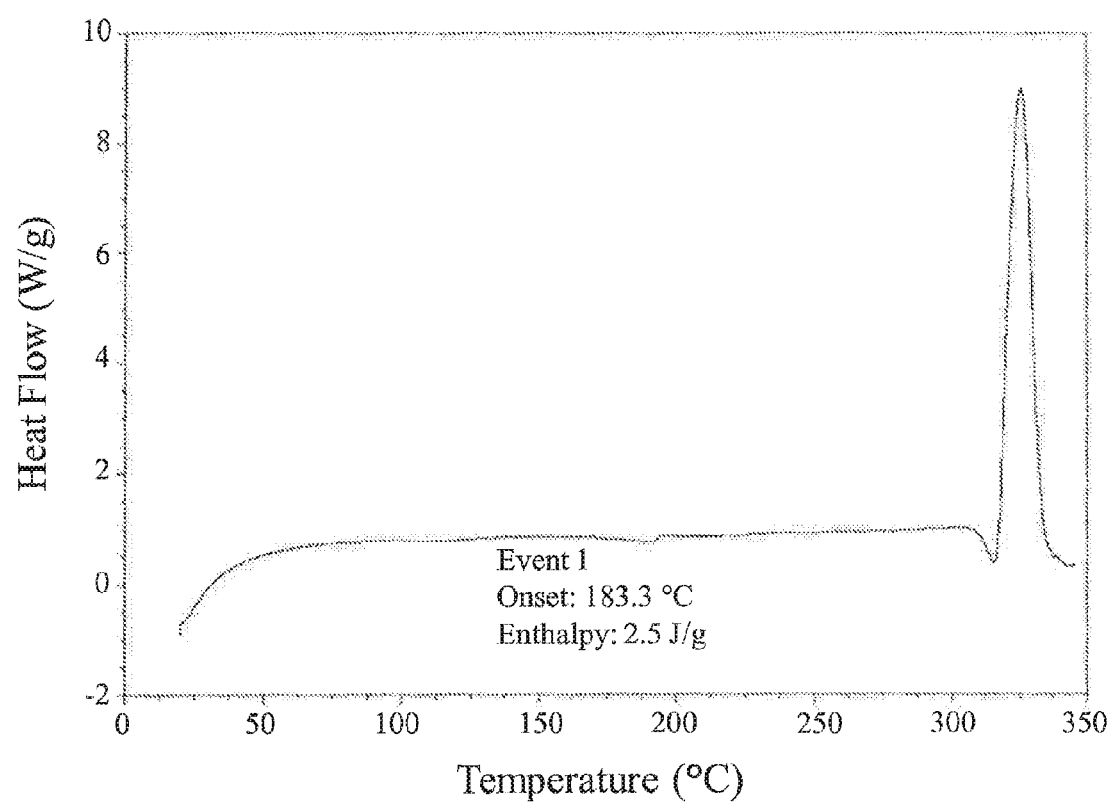
FIG. 13 shows a differential scanning calorimetry trace of Compound A—desolvated crystalline form.
Figure 17:
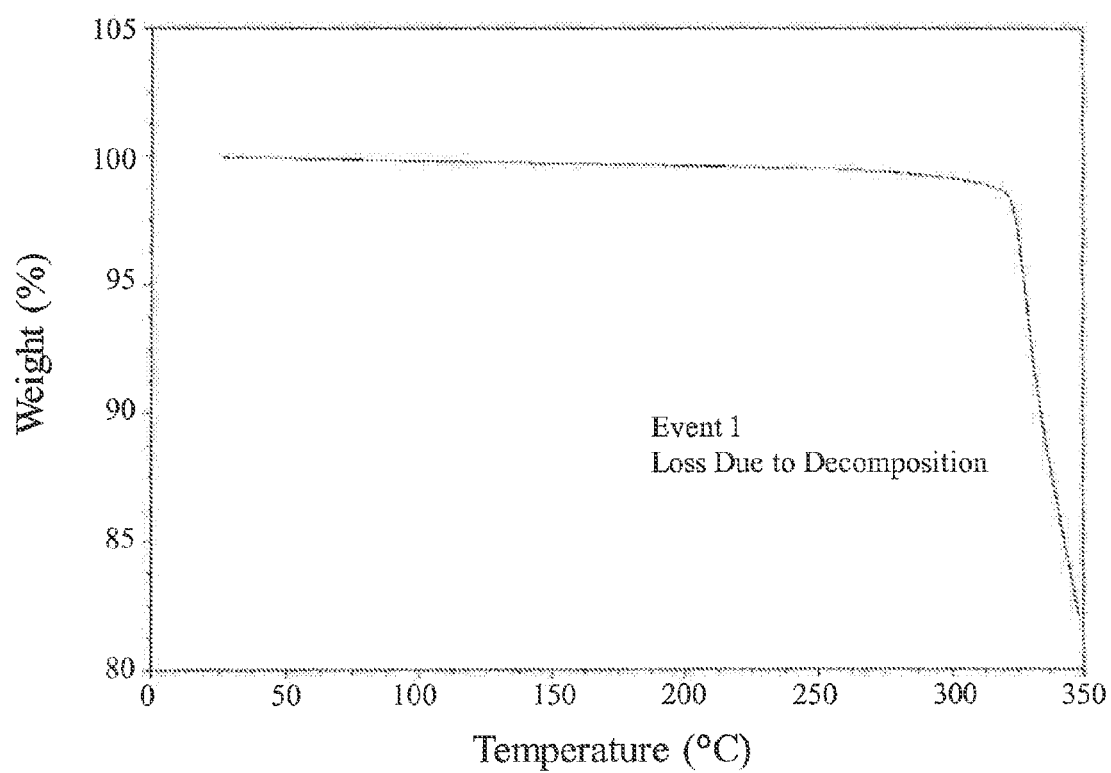
FIG. 17 shows a thermogravimetric analysis trace of Compound A—desolvated crystalline form.

Another embodiment of the present invention is directed to Compound A—desolvated crystalline form, wherein the crystalline form provides a differential scanning calorimetry trace substantially in accordance with FIG. 13 and/or a thermogravimetric analysis trace substantially in accordance with FIG. 17.

Another embodiment of the present invention is directed to a crystalline sodium salt of 4-tert-butyl-N-[4-chloro-2-(1-oxy-pyridine-4-carbonyl)-phenyl]-benzenesulfonamide (hereinafter "Compound A—hydrate"), wherein the crystalline form is characterized by an X-ray powder diffraction pattern comprising diffraction angles (°2θ), when measured using Cu K$_\alpha$ radiation, at about 6.1, 12.4, 15.9, 16.4, 16.9, 17.8, 18.0, 19.1, 23.4, and 25.0.

Figure 5:
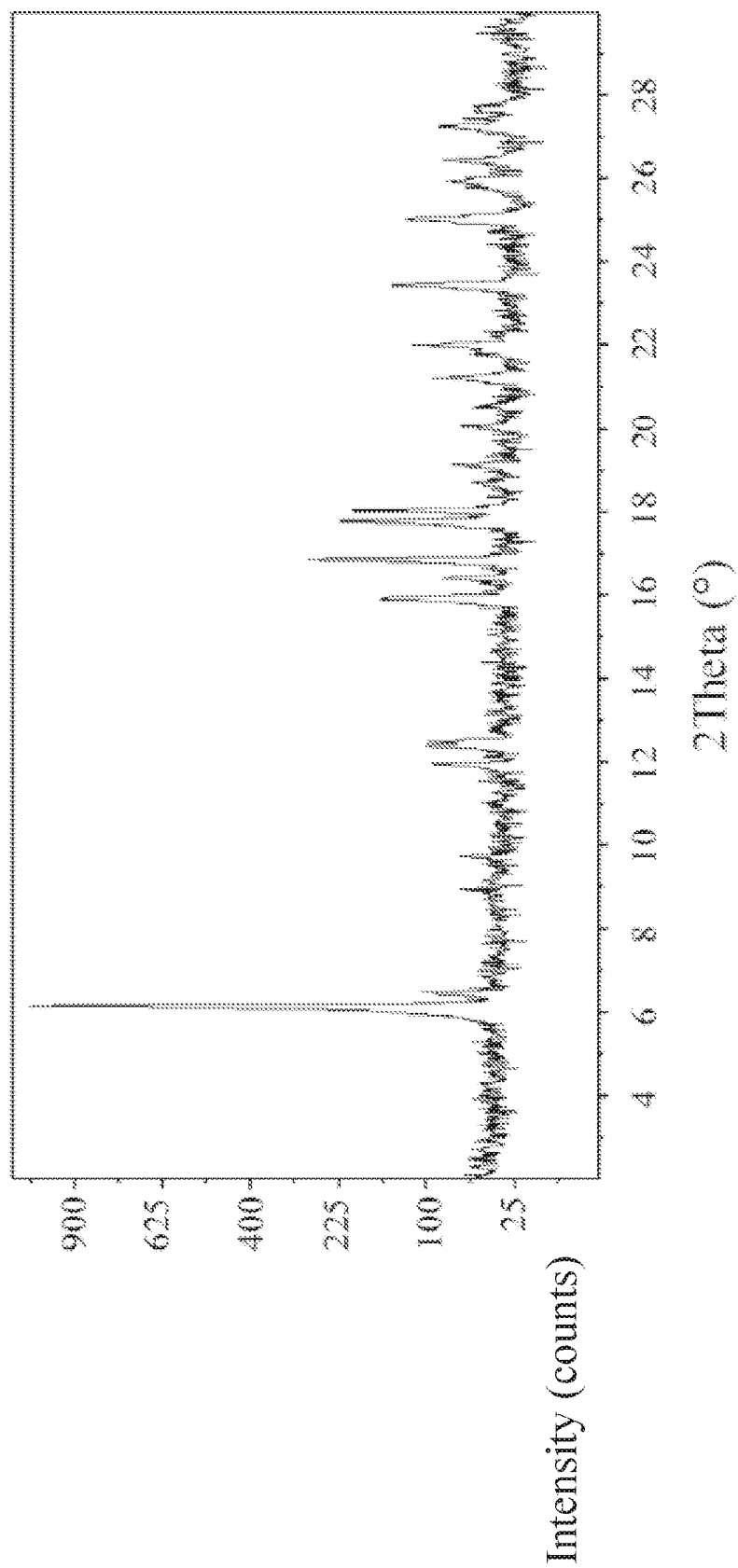
FIG. 5 shows an X-ray powder diffraction pattern of Compound A—hydrate.

Another embodiment of the present invention is directed to Compound A—hydrate, wherein the crystalline form is characterized by an X-ray powder diffraction pattern substantially in accordance with FIG. 5.

Figure 18:
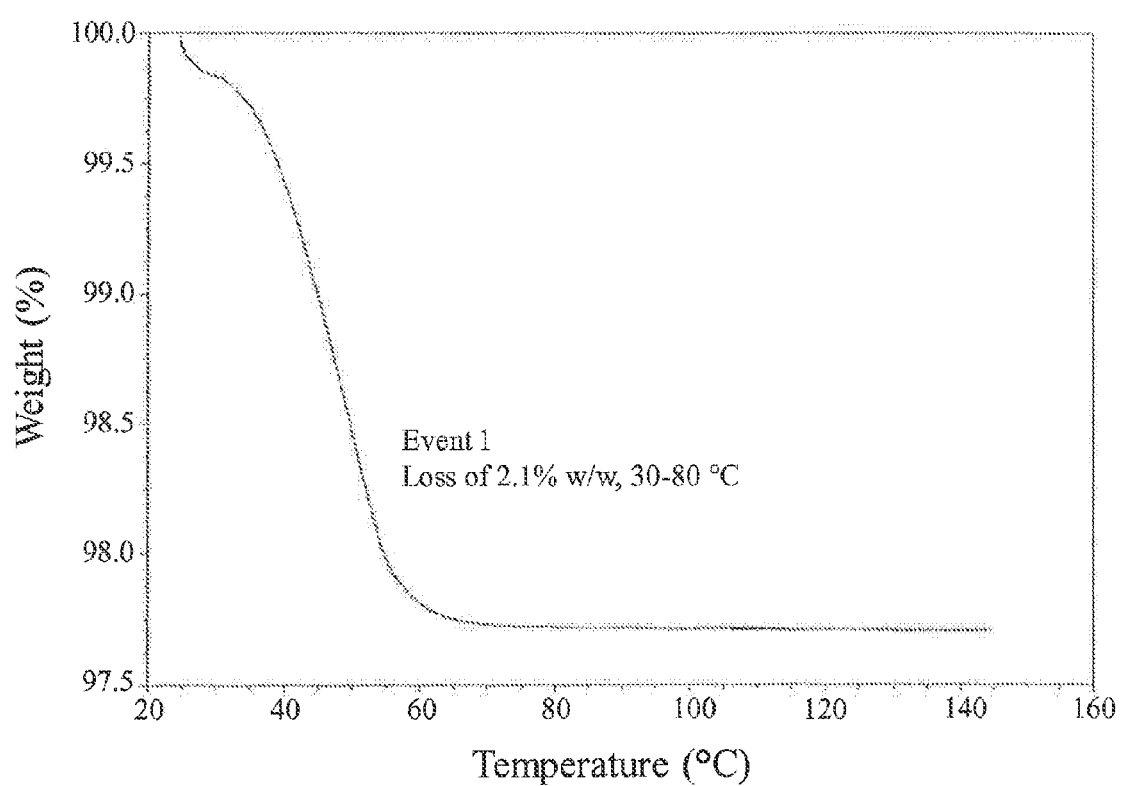
FIG. 18 shows a thermogravimetric analysis trace of Compound A—hydrate.

Another embodiment of the present invention is directed to Compound A—hydrate, wherein the crystalline form provides a thermogravimetric analysis trace substantially in accordance with FIG. 18.

It is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1, 2, 3, 4, or 5 provided herein is an XRPD pattern that would be considered by one skilled in the art to represent a compound possessing the same crystal form as the compound that provided the XRPD pattern of FIG. 1, 2, 3, 4, or 5. That is, the XRPD pattern may be identical to that of FIG. 1, 2, 3, 4, or 5, or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of a sodium salt of 4-tert-butyl-N-[4-chloro-2-(1-oxy-pyridine-4-carbonyl)-phenyl]-benzenesulfonamide, with FIG. 1 and, using expertise and knowledge in the art, readily determine whether the XRPD pattern of the sample is substantially in accordance with the XRPD pattern of Compound A—1,4-dioxane/water solvate. If the XRPD pattern is substantially in accordance with FIG. 1, the sample form can be readily and accurately identified as having the same form as Compound A—1,4-dioxane/water solvate. Similarly, a person skilled in the art is capable of determining if a given diffraction angle (expressed in °2θ) obtained from an XRPD pattern is at about the same position as a value presented herein.

"A compound of the invention" means a sodium salt of 4-tert-butyl-N-[4-chloro-2-(1-oxy-pyridine-4-carbonyl)-phenyl]-benzenesulfonamide, specifically the crystalline forms defined herein as Compound A—1,4-dioxane/water solvate, Compound A—formamide solvate, Compound A—dimethylsulfoxide solvate, Compound A—desolvated crystalline form, and Compound A—hydrate.

The invention includes a therapeutic method for treating or ameliorating a CCR9-mediated disorder in a subject in need thereof comprising administering to a subject in need thereof an effective amount of a compound of the invention or a composition comprising an effective amount of a compound of the invention and an optional pharmaceutically acceptable carrier.

As used herein, the phrase "CCR9-mediated disorder" and related phrases and terms refer to a condition or disease characterized by inappropriate, i.e., less than or greater than normal, CCR9 functional activity. Inappropriate CCR9 functional activity might arise as the result of CCR9 expression in cells which normally do not express CCR9, increased CCR9 expression (leading to, e.g., inflammatory and immunoregulatory disorders and diseases) or decreased CCR9 expression. Inappropriate CCR9 functional activity might also arise as the result of TECK secretion by cells which normally do not secrete TECK, increased TECK expression (leading to, e.g., inflammatory and immunoregulatory disorders and diseases) or decreased TECK expression. A CCR9-mediated disorder may be completely or partially mediated by inappropriate CCR9 functional activity. However, a CCR9-mediated disorder is one in which modulation of CCR9 results in some effect on the underlying condition or disease (e.g., a CCR9 antagonist results in some improvement in patient well being in at least some patients).

"Effective amount" means that amount of drug substance (i.e. a compound of the present invention) that elicits the desired biological response in a subject. Such response includes alleviation of the symptoms of the disease or disorder being treated. The effective amount of a compound of the invention in such a therapeutic method is about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It is to be understood, however, that the specific dose level and frequency of dosage for any particular patient may be varied and will depend upon a variety of factors including age, body weight, hereditary characteristics, general health, gender, diet, mode and time of administration, rate of excretion, drug combination, and the nature and severity of the particular condition being treated.

Administration methods include administering an effective amount of a compound or composition of the invention at different times during the course of therapy or concurrently in a combination form. The methods of the invention include all known therapeutic treatment regimens.

Diseases and conditions associated with inflammation, immune disorders, infection and cancer may be treated or prevented with the present compounds, compositions, and methods. In one group of embodiments, diseases or conditions, including chronic diseases, of humans or other species can be treated with an inhibitor of CCR9 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathics, (7) seleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) pulmonary fibrosis and other fibrotic diseases, and (14) irritable bowel syndrome.

Preferably, the present methods are directed to the treatment of diseases or conditions selected from inflammatory bowel disease, including Crohn's disease and ulcerative colitis; allergic diseases such as psoriasis, atopic dermatitis, and asthma; and autoimmune diseases such as rheumatoid arthritis.

More preferably, the present methods are directed to the treatment of inflammatory bowel disease, including Crohn's disease and ulcerative colitis.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

The weight ratio of a compound of the present invention to the second active ingredient may be varied and will depend upon the effective dose of each ingredient. Generally, an effective dose of each will be used. Thus, for example, when a compound of the present invention is combined with an NSAID the weight ratio of a compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Combination therapy includes co-administration of a compound of the invention and said other agent, sequential administration of a compound of the invention and the other agent, administration of a composition containing a compound of the invention and the other agent, or simultaneous administration of separate compositions containing a compound of the invention and the other agent.

The invention further includes the use of a compound of the invention as an active therapeutic substance, in particular in the treatment of CCR9-mediated disorders. In particular, the invention includes the use of a compound of the invention in the treatment of inflammatory bowel disease, including Crohn's disease and ulcerative colitis.

In another aspect, the invention includes the use of compounds of the invention in the manufacture of a medicament for use in the treatment of the above disorders.

"Pharmaceutically acceptable carrier" means any one or more compounds and/or compositions that are of sufficient purity and quality for use in the formulation of a compound of the invention that, when appropriately administered to a human, do not produce an adverse reaction, and that are used as a vehicle for a drug substance (i.e. a compound of the present invention).

The invention further includes the process for making the composition comprising mixing a compound of the invention and an optional pharmaceutically acceptable carrier; and includes those compositions resulting from such a process, which process includes conventional pharmaceutical techniques. For example, a compound of the invention may be nanomilled prior to formulation. A compound of the invention may also be prepared by grinding, micronizing or other particle size reduction methods known in the art. Such methods include, but are not limited to, those described in U.S. Pat. Nos. 4,826,689, 5,145,684, 5,298,262, 5,302,401, 5,336,507, 5,340,564, 5,346,702, 5,352,459, 5,354,560, 5,384,124, 5,429,824, 5,503,723, 5,510,118, 5,518,187, 5,518,738, 5,534,270, 5,536,508, 5,552,160, 5,560,931, 5,560,932, 5,565,188, 5,569,448, 5,571,536, 5,573,783, 5,580,579, 5,585,108, 5,587,143, 5,591,456, 5,622,938, 5,662,883, 5,665,331, 5,718,919, 5,747,001, PCT applications WO 93/25190, WO 96/24336, and WO 98/35666, each of which is incorporated herein by reference. The pharmaceutical compositions of the invention may be prepared using techniques and methods known to those skilled in the art. Some of the methods commonly used in the art are described in *Remington's Pharmaceutical Sciences* (Mack Publishing Company), the entire teachings of which are incorporated herein by reference.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders.

The oral composition is preferably formulated as a homogeneous composition, wherein the drug substance (i.e. a compound of the present invention) is dispersed evenly throughout the mixture, which may be readily subdivided into dosage units containing equal amounts of a compound of the invention. Preferably, the compositions are prepared by mixing a compound of the invention with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binding agents include starch, gelatin, natural sugars (e.g. glucose and beta-lactose), corn sweeteners and natural and synthetic gums (e.g. acacia and tragacanth). Disintegrating agents include starch, methyl cellulose, agar, and bentonite.

A compound of the invention may also be administered via a delayed release composition, wherein the composition includes a compound of the invention and a biodegradable slow release carrier (e.g. a polymeric carrier) or a pharmaceutically acceptable non-biodegradable slow release carrier (e.g. an ion exchange carrier).

Biodegradable and non-biodegradable delayed release carriers are well known in the art. Biodegradable carriers are used to form particles or matrices which retain a drug substance(s) (i.e. a compound of the present invention) and which slowly degrade/dissolve in a suitable environment (e.g. aqueous, acidic, basic and the like) to release the drug substance(s). Such particles degrade/dissolve in body fluids to release the drug substance(s) (i.e. compounds of the present invention) therein. The particles are preferably nanoparticles (e.g. in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and a compound of the invention.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Without further elaboration, it is believed that one skilled in the art can, using the preceding description, utilize the present invention to its fullest extent. The following Examples are, therefore, to be construed as merely illustrative and not a limitation of the scope of the present invention in any way.

Example 1

Preparation of: An anhydrous crystalline sodium salt of 4-tert-butyl-N-[4-chloro-2-(1-oxy-pyridine-4-carbonyl)-phenyl]-benzenesulfonamide A reaction vessel was charged with 300 g 4-tert-butyl-N-[4-chloro-2-(1-oxy-pyridine-4-carbonyl)-phenyl]-benzenesulfonamide, 4.737 mL Industrial Methylated Spirits (IMS), and 302.4 mL water. 27.245 g sodium hydroxide pellets were added to the slurry at 25° C. The reaction mixture was agitated at ambient temperature for 50 minutes, followed by heating to ~78° C. to dissolve all solids. The clear solution was then filtered while maintaining the temperature above 55° C. throughout the filtration process. After filtration, the filtered solution was reheated to 75° C. and then cooled to 55° C. and seeded with 3.0 g Compound B—anhydrous crystalline form (prepared by an analogous procedure) as a slurry in 15 mL IMS at ambient temperature. The slurry was held at 55° C. overnight and then cooled to 45° C. Vacuum distillation was employed while heating the reactor jacket to 65° C. and not allowing the slurry temperature to exceed 55° C., leaving ~1,500 mL of slurry in the reactor. The slurry was cooled to −10° C., held at that temperature overnight, and then transferred to a filter dryer and settled for 10 minutes. The jacket temperature of the filter was pre-chilled to −10° C. The mother liquors were removed to breakthrough using 0.5 to 1 bar nitrogen pressure. The crystallizer was charged with a first pre-chilled wash of 1,200 mL IMS, chilled to −10° C. The wash was transferred to the cake in the filter, agitated for 10 minutes, settled for 10 minutes, and removed under 0.5 to 1 bar nitrogen pressure. The washing of the filter cake was repeated two additional times under the same conditions. The jacket temperature of the filter was increased to 20° C. and the cake was blown-down under 0.5 to 1 bar nitrogen pressure until the solvent being removed was reduced to a trickle. The wet cake was dried at 70° C. with agitation under vacuum to provide 258.3 g of the title compound as a yellow crystalline solid.

Example 2

Preparation of: A crystalline sodium salt of 4-tert-butyl-N-[4-chloro-2-(1-oxy-pyridine-4-carbonyl)-phenyl]-benzenesulfonamide (Compound A—1,4-dioxane/water solvate)

100 mg of an anyhydrous crystalline sodium salt of 4-tert-butyl-N-[4-chloro-2-(1-oxy-pyridine-4-carbonyl)-phenyl]-benzenesulfonamide was weighed into a 1.8-mL vial containing a stir bar. Water (43.9 μL), 1,4-dioxane (53.0 μL), and 1 M sodium hydroxide (4.3 μL) were added, the vial was tightly capped, and the solution was stirred for 5 days at 25° C. The resulting solid was isolated using a Büchner funnel, and the filter cake was air-dried for 1 hour to provide the title compound as a yellow solid.

The X-ray powder diffraction (XRPD) pattern of this material is shown in FIG. 1 and a summary of the diffraction angles and d-spacings is given in Table I. The XRPD analysis was conducted on a PANanalytical X'Pert Pro Diffractometer, model PW3040/60, serial number DY2407 using an X'Celerator detector. The acquisition conditions included: Cu K$_\alpha$ radiation (λ=1.54059 Å), generator tension: 45 kV, generator current: 40 mA, start angle: 2.0°2θ, end angle: 50.0°2θ, step size: 0.0167°2θ, time per step: 40.005 seconds. The sample was prepared using zero background (front fill) technique.

TABLE I

| Diff. Angle [°2θ] | d-spacing [Å] |
|---|---|
| 4.0111 | 22.01079 |
| 8.0656 | 10.95305 |
| 10.0893 | 8.76019 |
| 14.1627 | 6.24847 |
| 16.197 | 5.46795 |
| 18.6342 | 4.75791 |
| 20.3118 | 4.36857 |
| 24.6832 | 3.60392 |
| 24.9557 | 3.56518 |
| 26.5095 | 3.35963 |

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 6 with major peaks observed at 668, 743, 804, 1125, 1154, 1162, 1286, 1544, 1587, 1597, 1611, 1657, and 1672 cm$^{-1}$.

The differential scanning calorimetry (DSC) thermogram of the title compound was recorded on a TA Instruments Q1000 Differential Scanning Calorimeter and is shown in FIG. 10. The sample was weighed into an aluminium pan, a pan lid placed on top and lightly crimped without sealing the pan. The experiments were conducted using a heating rate of 15° C./min.

The thermogravimetric analysis (TGA) thermogram of the title compound was recorded on a TA Instruments Q5000 Themrogravimetric Analyzer and is shown in FIG. 14. The experiments were conducted using a heating rate of 15° C./min.

Example 3

Preparation of: A crystalline sodium salt of 4-tert-butyl-N-[4-chloro-2-(1-oxy-pyridine-4-carbonyl)-phenyl]-benzenesulfonamide (Compound A—formamide solvate)

300 mg of an anyhydrous crystalline sodium salt of 4-tert-butyl-N-[4-chloro-2-(1-oxy-pyridine-4-carbonyl)-phenyl]-benzenesulfonamide was weighed into a 4-mL vial containing a stir bar. Dichloromethane (1,050 μL), formamide (450 μL), and 0.5 M sodium methoxide (38.4 μL) were added sequentially. The suspension was heated to 40° C. and stirred for 30 minutes. The sample was cooled to 0° C. at 1° C./minute and then stirred for an additional 30 minutes. The resulting solid was isolated using a Büchner funnel, and the filter cake was washed with cold dichloromethane (4 mL, pre-cooled to 1° C.), and dried at 50° C. for 30 minutes to provide the title compound as a yellow solid.

The X-ray powder diffraction (XRPD) pattern of this material is shown in FIG. 2 and a summary of the diffraction angles and d-spacings is given in Table II. The XRPD analysis was conducted on a PANanalytical X'Pert Pro Diffractometer, model PW3040/60, serial number DY2407 using an X'Celerator detector. The acquisition conditions included: Cu K$_\alpha$ radiation (λ=1.54059 Å), generator tension:

45 kV, generator current: 40 mA, start angle: 2.0°2θ, end angle: 50.0°2θ, step size: 0.0167°2θ, time per step: 40.005 seconds. The sample was prepared using zero background (front fill) technique.

TABLE II

| Diff. Angle [°2θ] | d-spacing [Å] |
|---|---|
| 5.878 | 15.02355 |
| 8.6404 | 10.22566 |
| 12.0513 | 7.33805 |
| 12.6593 | 6.98695 |
| 16.125 | 5.4922 |
| 16.9097 | 5.23907 |
| 17.4114 | 5.08922 |
| 17.7555 | 4.99136 |
| 18.0075 | 4.92206 |
| 20.3906 | 4.35187 |
| 20.6226 | 4.30343 |
| 21.7359 | 4.08548 |
| 22.5655 | 3.93711 |
| 23.749 | 3.74352 |
| 23.8983 | 3.72046 |
| 24.2996 | 3.65992 |
| 25.8941 | 3.43805 |
| 26.2873 | 3.38752 |
| 26.5418 | 3.35561 |
| 26.8984 | 3.31193 |
| 27.9099 | 3.19415 |
| 30.8679 | 2.89447 |
| 38.6418 | 2.32818 |

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 7 with major peaks observed at 655, 668, 737, 804, 1079, 1099, 1123, 1161, 1229, 1303, 1465, 1537, 1595, 1611, and 1654 cm$^{-1}$.

The differential scanning calorimetry (DSC) thermogram of the title compound was recorded on a TA Instruments Q1000 Differential Scanning Calorimeter and is shown in FIG. 11. The sample was weighed into an aluminium pan, a pan lid placed on top and lightly crimped without sealing the pan. The experiments were conducted using a heating rate of 15° C./min.

The thermogravimetric analysis (TGA) thermogram of the title compound was recorded on a TA Instruments Q5000 Themrogravimetric Analyzer and is shown in FIG. 15. The experiments were conducted using a heating rate of 15° C./min.

Example 4

Preparation of: A crystalline sodium salt of 4-tert-butyl-N-[4-chloro-2-(1-oxy-pyridine-4-carbonyl)-phenyl]-benzenesulfonamide (Compound A—dimethylsulfoxide solvate)

100 mg of an anyhydrous crystalline sodium salt of 4-tert-butyl-N-[4-chloro-2-(1-oxy-pyridine-4-carbonyl)-phenyl]-benzenesulfonamide was weighed into a 2-mL vial containing a stir bar. Chlorobenzene (350 µL), dimethylsulfoxide (150 µL), and 0.5 M sodium methoxide (12.5 µL) were added sequentially. The suspension was stirred at 25° C. for 3 weeks. The resulting solid was isolated on filter paper, and the filter cake was dried at 40° C. for 2 hours to provide the title compound.

The X-ray powder diffraction (XRPD) pattern of this material is shown in FIG. 3 and a summary of the diffraction angles and d-spacings is given in Table III. The XRPD analysis was conducted on a PANanalytical X'Pert Pro Diffractometer, model PW3040/60, serial number DY2407 using an X'Celerator detector. The acquisition conditions included: Cu K$_\alpha$ radiation (λ=1.54059 Å), generator tension: 45 kV, generator current: 40 mA, start angle: 2.0°2θ, end angle: 50.0°2θ, step size: 0.0167°2θ, time per step: 40.005 seconds. The sample was prepared using zero background (front fill) technique.

TABLE III

| Diff. Angle [°2θ] | d-spacing [Å] |
|---|---|
| 5.5934 | 15.7874 |
| 7.9864 | 11.06143 |
| 10.7791 | 8.20108 |
| 15.6579 | 5.65498 |
| 16.9909 | 5.2142 |
| 17.7411 | 4.99539 |
| 17.9833 | 4.92863 |
| 18.1354 | 4.88764 |
| 18.4398 | 4.80765 |
| 21.2071 | 4.18612 |
| 21.7596 | 4.08107 |
| 22.5174 | 3.94542 |
| 22.7501 | 3.90558 |
| 24.2764 | 3.66338 |
| 28.5661 | 3.12225 |
| 29.694 | 3.00618 |
| 34.461 | 2.60046 |

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 8 with major peaks observed at 662, 672, 718, 729, 750, 799, 1078, 1109, 1158, 1236, 1302, 1536, 1588, 1596, and 1636 cm$^{-1}$.

The differential scanning calorimetry (DSC) thermogram of the title compound was recorded on a TA Instruments Q1000 Differential Scanning Calorimeter and is shown in FIG. 12. The sample was weighed into an aluminium pan, a pan lid placed on top and lightly crimped without sealing the pan. The experiments were conducted using a heating rate of 15° C./min.

The thermogravimetric analysis (TGA) thermogram of the title compound was recorded on a TA Instruments Q5000 Themrogravimetric Analyzer and is shown in FIG. 16. The experiments were conducted using a heating rate of 15° C./min.

Example 5

Preparation of: A crystalline sodium salt of 4-tert-butyl-N-[4-chloro-2-(1-oxy-pyridine-4-carbonyl)-phenyl]-benzenesulfonamide (Compound A—desolvated crystalline form)

100 mg of a crystalline formamide solvate of a sodium salt of 4-tert-butyl-N-[4-chloro-2-(1-oxy-pyridine-4-carbonyl)-phenyl]-benzenesulfonamide (Compound A—formamide solvate) was placed onto an aluminum TGA pan and heated to 260° C. at a rate of 15° C./minute using a TA Instruments Q5000 Themrogravimetric Analyzer to provide the title compound.

The X-ray powder diffraction (XRPD) pattern of this material is shown in FIG. 4 and a summary of the diffraction angles and d-spacings is given in Table IV. The XRPD analysis was conducted on a PANanalytical X'Pert Pro Diffractometer, model PW3040/60, serial number DY2407 using an X'Celerator detector. The acquisition conditions included: Cu K$_\alpha$ radiation ($\lambda$=1.54059 Å), generator tension: 45 kV, generator current: 40 mA, start angle: 2.0°2θ, end angle: 50.0°2θ, step size: 0.0167°2θ, time per step: 40.005 seconds. The sample was prepared using zero background (front fill) technique.

TABLE IV

| Diff. Angle [°2θ] | d-spacing [Å] |
|---|---|
| 6.4791 | 13.63095 |
| 9.586 | 9.21894 |
| 10.6185 | 8.32478 |
| 11.9048 | 7.42802 |
| 14.4414 | 6.12848 |
| 16.0781 | 5.50811 |
| 17.6985 | 5.0073 |
| 17.9351 | 4.94178 |
| 19.3172 | 4.59121 |
| 21.0851 | 4.21008 |
| 21.9857 | 4.03961 |
| 22.2374 | 3.99444 |
| 23.3765 | 3.80232 |
| 23.6316 | 3.76185 |
| 24.432 | 3.64039 |
| 26.2667 | 3.39013 |
| 27.7153 | 3.21614 |
| 28.5025 | 3.12908 |
| 29.5187 | 3.02363 |

The Raman spectrum of the title compound was recorded on a Nicolet NXR 9650 FT-Raman Spectrometer, at 4 cm$^{-1}$ resolution with excitation from a Nd:YVO4 laser ($\lambda$=1064 nm). The Raman spectrum of this material is shown in FIG. 9 with major peaks observed at 654, 667, 737, 803, 855, 1077, 1122, 1160, 1311, 1461, 1536, 1592, 1609, and 1648 cm$^{-1}$.

The differential scanning calorimetry (DSC) thermogram of the title compound was recorded on a TA Instruments Q1000 Differential Scanning Calorimeter and is shown in FIG. 13. The sample was weighed into an aluminium pan, a pan lid placed on top and lightly crimped without sealing the pan. The experiments were conducted using a heating rate of 15° C./min.

The thermogravimetric analysis (TGA) thermogram of the title compound was recorded on a TA Instruments Q5000 Themrogravimetric Analyzer and is shown in FIG. 17. The experiments were conducted using a heating rate of 15° C./min.

Example 6

Preparation of: A crystalline sodium salt of 4-tert-butyl-N-[4-chloro-2-(1-oxy-pyridine-4-carbonyl)-phenyl]-benzenesulfonamide (Compound A—hydrate)

Approximately 30 mg of a desolvated crystalline form of a sodium salt of 4-tert-butyl-N-[4-chloro-2-(1-oxy-pyridine-4-carbonyl)-phenyl]-benzenesulfonamide (Compound A—desolvated crystalline form) placed on a flat XRPD sample holder and left standing in a fume hood for 5 weeks to provide the title compound mixed with some of the starting desolvated material.

The X-ray powder diffraction (XRPD) pattern of this material is shown in FIG. 5 and a summary of the diffraction angles and d-spacings is given in Table V. The XRPD analysis was conducted on a PANanalytical X'Pert Pro Diffractometer, model PW3040/60, serial number DY2407 using an X'Celerator detector. The acquisition conditions included: Cu K$_\alpha$ radiation ($\lambda$=1.54059 Å), generator tension: 45 kV, generator current: 40 mA, start angle: 2.0°2θ, end angle: 50.0°2θ, step size: 0.0167°2θ, time per step: 40.005 seconds. The sample was prepared using zero background (front fill) technique.

TABLE V

| Diff. Angle [°2θ] | d-spacing [Å] |
|---|---|
| 6.1432 | 14.37558 |
| 12.3809 | 7.14337 |
| 15.9257 | 5.56049 |
| 16.4099 | 5.39747 |
| 16.8501 | 5.25745 |
| 17.7646 | 4.98883 |
| 18.0388 | 4.9136 |
| 19.126 | 4.63667 |
| 23.443 | 3.79169 |
| 25.0165 | 3.55664 |

The thermogravimetric analysis (TGA) thermogram of the product was recorded on a TA Instruments Q5000 Themrogravimetric Analyzer and is shown in FIG. 18. The experiments were conducted using a heating rate of 15° C./min.

What is claimed is:

1. A crystalline form of a sodium salt of 4-tert-butyl-N-[4-chloro-2-(1-oxy-pyridine-4-carbonyl)-phenyl]-benzenesulfonamide, wherein the crystalline form is characterized by an X-ray powder diffraction pattern substantially in accordance with FIG. 3.

2. A crystalline form of a sodium salt of claim 1, wherein the crystalline form is characterized by an X-ray powder diffraction pattern containing diffraction angles, when measured using Cu K$_\alpha$ radiation, at about 5.6, 17.7, 22.8, 24.3, 28.6, and 34.5° 2θ.

3. The crystalline form of claim 1, wherein the crystalline form provides a Raman spectrum containing peaks at about 718, 1158, 1302, 1588, 1596, and 1636 cm$^{-1}$.

4. The crystalline form of claim 1, wherein the crystalline form provides a Raman spectrum substantially in accordance with FIG. 8.

5. A pharmaceutical composition comprising the crystalline form of claim 1 and a pharmaceutically acceptable carrier.

6. A method of preparing a pharmaceutical composition comprising admixing the crystalline form of claim 1 and a pharmaceutically acceptable carrier.

7. The crystalline form of claim 1, wherein the crystalline form differential scanning calorimetry thermogram profile is substantially in accordance with FIG. 12.

* * * * *